(12) United States Patent
Cole et al.

(10) Patent No.: US 11,344,440 B2
(45) Date of Patent: May 31, 2022

(54) ENDOGRAFT VISUALIZATION WITH PRE-INTEGRATED OR REMOVABLE OPTICAL SHAPE SENSING ATTACHMENTS

(71) Applicant: KONINKLIJKE PHILIPS N.V., Eindhoven (NL)

(72) Inventors: Gregory Cole, Ossining, NY (US); Molly Lara Flexman, Melrose, MA (US); David Paul Noonan, New York, NY (US); Neriman Nicoletta Kahya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 491 days.

(21) Appl. No.: 15/544,527

(22) PCT Filed: Jan. 7, 2016

(86) PCT No.: PCT/IB2016/050054
§ 371 (c)(1),
(2) Date: Jul. 19, 2017

(87) PCT Pub. No.: WO2016/116823
PCT Pub. Date: Jul. 28, 2016

(65) Prior Publication Data
US 2018/0008443 A1    Jan. 11, 2018

Related U.S. Application Data

(60) Provisional application No. 62/106,260, filed on Jan. 22, 2015.

(51) Int. Cl.
*A61F 2/954* (2013.01)
*A61F 2/07* (2013.01)
(Continued)

(52) U.S. Cl.
CPC .............. *A61F 2/954* (2013.01); *A61B 34/20* (2016.02); *A61F 2/07* (2013.01); *A61F 2/91* (2013.01); *G01B 11/24* (2013.01); *A61B 2034/2055* (2016.02); *A61B 2034/2061* (2016.02); *A61F 2/82* (2013.01); *A61F 2002/065* (2013.01);
(Continued)

(58) Field of Classification Search
CPC ...... A61F 2/07; A61F 2210/0014; A61F 2/82; A61F 2220/075; A61F 2250/096; A61F 2034/2061; A61F 2/91; A61F 2/954; A61F 2002/065; A61F 2002/072; A61B 34/20; A61B 2034/2061; A61B 2034/2055; G01B 11/24
See application file for complete search history.

(56) References Cited

U.S. PATENT DOCUMENTS 6,168,615 B1   1/2001   Ken et al.
8,057,399 B2   11/2011  Greenland et al.
(Continued)

FOREIGN PATENT DOCUMENTS

EP   0997115 A2   5/2000
JP   4194852 A    9/2003

*Primary Examiner* — George J Ulsh

(57) ABSTRACT

An endograft (102) includes a stent structure. An optical shape sensing (OSS) system (104) is associated with the endograft and is configured to measure shape, position and/or orientation of the stent structure. The OSS system (104) is connected to the stent structure and removable in a plurality of ways. Methods for deployment and removal of the OSS system are also provided.

15 Claims, 7 Drawing Sheets

(51) Int. Cl.
 *A61B 34/20* (2016.01)
 *G01B 11/24* (2006.01)
 *A61F 2/91* (2013.01)
 *A61F 2/82* (2013.01)
 *A61F 2/06* (2013.01)

(52) U.S. Cl.
 CPC . *A61F 2002/072* (2013.01); *A61F 2210/0014* (2013.01); *A61F 2220/0075* (2013.01); *A61F 2250/0096* (2013.01)

(56) References Cited

U.S. PATENT DOCUMENTS

| | | |
|---|---|---|
| 8,123,796 B2 | 2/2012 | Kasprzak |
| 8,473,030 B2 | 6/2013 | Greenan |
| 9,636,040 B2 | 5/2017 | Duindam |
| 9,918,659 B2 | 3/2018 | Chopra |
| 10,390,889 B2 | 8/2019 | Sobe |
| 2005/0154417 A1 | 7/2005 | Sepetka et al. |
| 2007/0167911 A1 | 7/2007 | Gandhi et al. |
| 2007/0244547 A1 | 10/2007 | Greenan |
| 2008/0189921 A1 | 8/2008 | Tomosue |
| 2009/0177261 A1 | 7/2009 | Teoh et al. |
| 2009/0228020 A1 | 9/2009 | Wallace |
| 2012/0041534 A1 | 2/2012 | Clerc et al. |
| 2012/0191086 A1 | 7/2012 | Moll et al. |
| 2013/0028554 A1 | 1/2013 | Wong et al. |
| 2013/0281990 A1 | 10/2013 | Manzke et al. |
| 2014/0180126 A1 | 6/2014 | Millett et al. |
| 2016/0081760 A1 | 3/2016 | Verard |
| 2016/0242854 A1 | 8/2016 | Grass et al. |

ENDOGRAFT VISUALIZATION WITH PRE-INTEGRATED OR REMOVABLE OPTICAL SHAPE SENSING ATTACHMENTS

CROSS-REFERENCE TO PRIOR APPLICATIONS

This application is the U.S. National Phase application under 35 U.S.C. § 371 of International Application Serial No. PCT/IB2016/050054, filed on Jan. 7, 2016, which claims the benefit of U.S. Application Ser. No. 62/106,260, filed on Jan. 22, 2015. These applications are hereby incorporated by reference herein.

BACKGROUND

Technical Field

This disclosure relates to medical instruments and more particularly to systems, devices and methods for endograft placement/deployment with shape sensing optical fibers pre-integrated or applied post-deployment in the endograft or into components and/or accessories.

Description of the Related Art

Optical shape sensing (OSS) uses light along a multicore optical fiber for device localization and navigation during surgical intervention. One principle involved makes use of distributed strain measurement in the optical fiber using characteristic Rayleigh backscatter or controlled grating patterns. The shape along the optical fiber begins at a specific point along the sensor, known as the launch point (or z=0), and the subsequent shape position and orientation are relative to that point. For meaningful clinical use, shape-sensed devices can be registered to an imaging frame of reference (such as a pre-operative computed tomography (CT) or a live fluoroscopy image).

Endovascular aneurysm repair (EVAR) has replaced open surgery as the most common technique for the repair of abdominal aortic aneurysms (AAA). The procedure is typically carried out under x-ray fluoroscopy guidance and uses significant amounts of contrast to position and deploy the stent graft correctly. On average 50-100 mL of contrast dye is used during an EVAR procedure, which may result in acute renal failure in rare cases.

The most common complication from EVAR is endoleaks resulting from an insufficient seal of the stent graft to the aorta. Endoleaks involve incorrect flow around the stent (for example, flow around the stent at the proximal or distal attachment site, flow through the graft wall, retrograde flow from the branches, etc.).

Another complication around EVAR involves ischemia of the aortic side branches (such as the colonic, renal, and pelvic arteries). This can occur due to misplacement of the stent graft such that the stent partially or completely covers one of the side vessels. This is associated with a lack of high-quality imaging technology as well as the experience of the endovascular team.

In EVAR, stent grafts are contained within a stent-deployment system that is used to navigate the endograft to the correct part of the vasculature. The deployment systems tend to be relatively large and stiff endovascular devices. They typically involve a handle or set of knobs and dials or wires at the proximal end to control the various steps around the stent deployment. The stent lies within a distal part of the device and is only released once the device has been navigated to the appropriate location. In some cases, the stent completely deploys in one step, while in other cases the stent can be partially deployed to allow for correct positioning and orientation before the final deployment step firmly attaches the stent to the vasculature (typically through a retaining/sealing ring).

The endovascular stent graft requires a sufficient amount of healthy vasculature where it can land its sealing ring. If this is not possible beneath the renal arteries, then the endograft will cover those arteries, and must create some alternative way of maintaining flow to those vessels. This can be done with a fenestrated stent (e.g., a stent with windows for the side-branches) in a procedure known as fenestrated endovascular aneurysm repair (FEVAR). In this case, the stent has fenestrations that must be lined up correctly with the side branches and additional stents are placed to connect the side vessels to the main stent.

Under x-ray guidance the endograft can be visualized through x-ray visible markers that are located in key positions on the endograft. In a fenestrated endograft, the markers identify the locations of the fenestrations and can be used to orient the stent to appropriately align the fenestrations with the side vessels. Complications from EVAR include misplacement of the endograft resulting in endoleaks, misplacement of the endograft resulting in occlusion of the side branches, contrast Nephropathy due to high levels of contrast used during endograft deployment and high contrast and radiation dose due to long procedure times due to navigation and deployment in a complex anatomy. In addition, placement of a three-dimensional stent within a three-dimensional anatomy is challenging and is typically performed under two-dimensional imaging guidance through x-ray fluoroscopy.

SUMMARY

In accordance with the present principles, an endograft includes a stent structure and at least one attachment mechanism configured to releasably attach to the stent structure. At least one optical shape sensing (OSS) system is coupled to the at least one attachment mechanism and is configured to measure at least one of shape, position or orientation of the stent structure.

Another endograft includes a stent structure and at least one deployable instrument pre-cannulated through a fenestration in the stent structure. The at least one deployable instrument includes an optical shape sensing (OSS) system and is configured to measure at least one of shape, position or orientation of the stent structure and align the fenestration with a branch of a blood vessel for placement of the endograft.

Yet another endograft includes a stent structure having a wall and a lumen formed within the wall of the stent structure. An optical shape sensing (OSS) system is configured to pass into the lumen, to be releasably secured to the stent structure and to be configured to measure at least one of shape, position or orientation of the stent structure.

Still another endograft includes a stent structure having a lumen with concentric supporting members and an eye formed within at least one of the concentric supporting members. An optical shape sensing (OSS) system is configured to pass through the eye, to be releasably secured to the stent structure and to be configured to measure at least one of shape, position or orientation of the stent structure.

A method for endograft deployment includes deploying at least one optical shape sensing (OSS) system associated with an endograft; measuring at least one of shape, position or orientation of the endograft during deployment using the at least one OSS system; registering OSS data with image data on a blood vessel where the endograft is placed; anchoring the endograft in the blood vessel; and removing at least a portion of the OSS system from the endograft.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
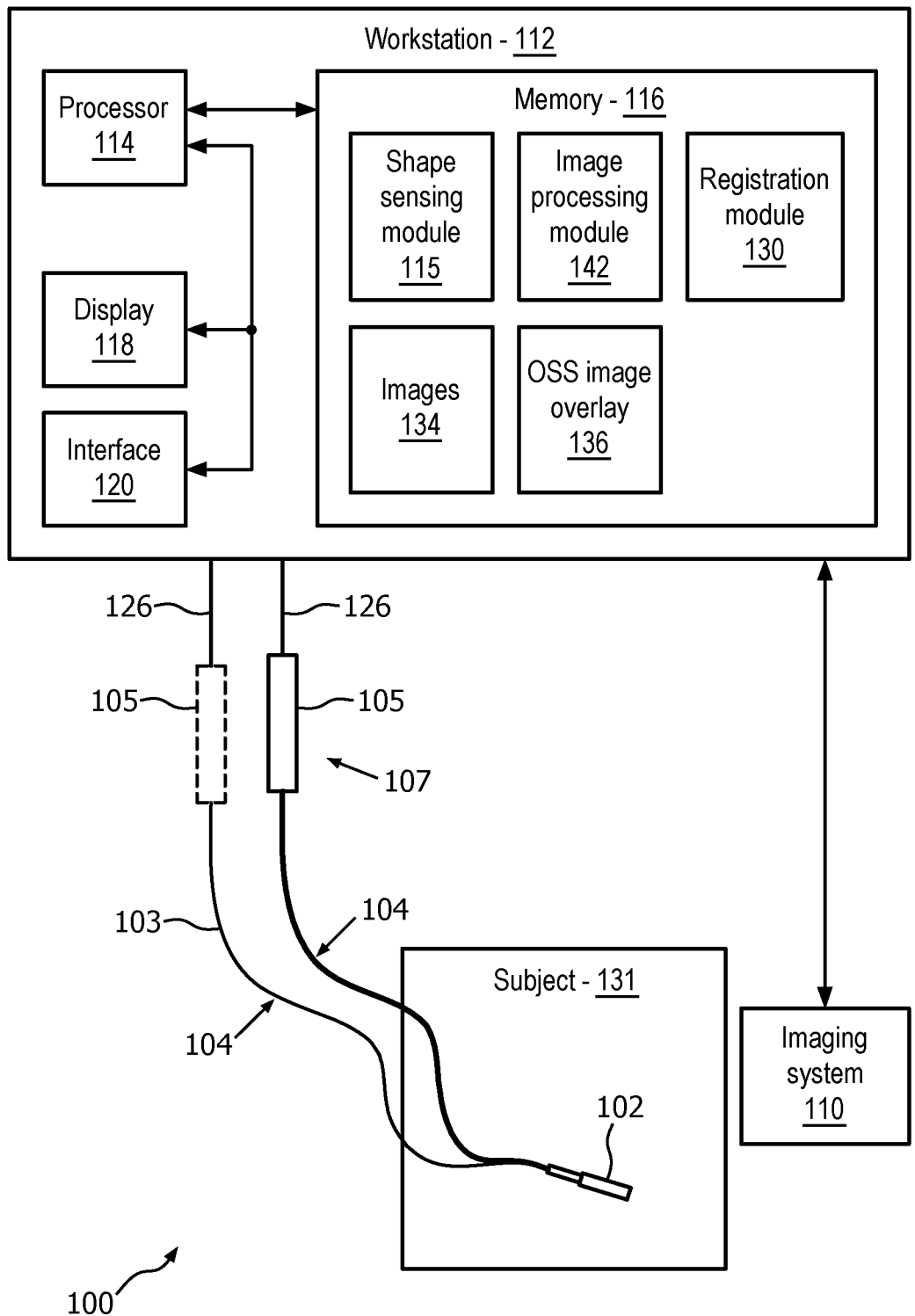
FIG. 1 is a block/flow diagram showing a system configured for endograft placement/deployment using an optical shape sensing system in accordance with one embodiment.

In accordance with the present principles, a three-dimensional visualization of a stent (endograft) with respect to anatomic imaging (e.g., a pre-operative computed tomography (CT) image, an intra-operative xperCT/3DRA, a fluoroscopy roadmap, ultrasound, etc.) can be more accurately controlled during deployment using optical shape sensing (OSS). Introducing OSS for navigation to endovascular aneurysm repair (EVAR) can reduce radiation dose and provide a more intuitive way to position catheters and guidewires within a three-dimensional vasculature to reduce procedure times and improve outcomes.

One feature of EVAR procedures is the deployment of an endograft. The orientation and position of the endograft is an important consideration in making a good seal with the vessel and adjusting the flow such that an aneurysm is no longer under pressure. If the endograft is not positioned correctly, blood may leak around the stent graft and continue to pool in an aneurysm sac, or the endograft could occlude side-vessels off the aorta which can cause poor blood flow to critical organs. In fenestrated endovascular aneurysm repair (FEVAR), side-branches (such as the renal arteries) need to be cannulated. This cannulation involves navigating a catheter and guidewire through a semi-deployed stent graft, exiting the stent graft via a fenestration, and then entering a target vessel. While this can be done through the known position and shape of the devices through OSS, it may also be advantageous to see the position of the endograft (and corresponding fenestrations). Thus, by shape sensing the endograft, the endograft position/orientation/shape can be tracked during deployment for optimal positioning and cannulation of side-vessels can be performed without (or with minimal) use of x-ray guidance. In one embodiment, guidance can be performed based on OSS-enabled devices, an OSS-enabled endograft, and a pre-operative CT/live fluoroscopy.

OSS-enabled endografts provide an operator with knowledge of the endograft shape and deformation and position of critical points on the endograft. The present principles pre-integrate or apply in-situ removable optical shape sensing devices on the endograft to provide enhanced visualization information during placement. To further provide the operator with knowledge of the endograft shape, position, and orientation, OSS guidance may be introduced into the endograft deployment process. Incorporating the shape sensing fiber directly into the deployment device/system may include modification of the design of an existing device or providing a new device. Alternatively, a clip or attachment mechanism that secures an OSS system to the endograft can attach directly to the endograft in one or multiple locations to permit visualization of the endograft. Visualization of the endograft can be complemented through the use of fluoroscopy or ultrasound imaging.

To introduce the use of OSS into an interventional procedure, the fiber needs to be integrated in the device used for the intervention. The optical fiber can be placed such that it does not interfere with the normal properties and functions of the device. This approach needs to consider the following. In small medical devices, it can be difficult to find a sufficiently large footprint of space available for a fiber and/or a lumen. Integrating the fiber into the wall can change the mechanical properties of the device.

In the case of endograft implantation, where it is important to maintain careful mechanical properties, it may be preferable to not interfere with the functional properties of the device. To accomplish useful and accurate visualization of the endograft during the deployment and anchoring process, without embedding fiber tracking into the endograft body itself, tracking several points on the endograft and endograft deployment system may be needed. By tracking or encoding handles of the deployment system, information about the endograft deployment status and orientation may also be determined. In addition, by tracking a tip position of the endograft deployment system, a 6 degree of freedom position of the anchor point of the endograft can clearly be determined. While these two approaches provide valuable information for endograft visualization, they may be too far removed from the structure that needs to be tracked, e.g., the deformable body of the endograft itself.

In some cases, it may not be suitable or possible to directly shape sense the entirety of the endograft. In such cases, the information may include a single position on the endograft, the position and orientation of a stiff guidewire, the position, orientation, and state of the deployment based on a handle of the deployment device used in conjunction with an OSS-enabled stiff guidewire, etc. To provide the operator with knowledge of the endograft shape, position, and orientation, it is possible to introduce optical shape sensing guidance to the endograft deployment process. In accordance with the present principles, mechanisms for aiding in the navigation, positioning, and alignment of the endograft are described.

The present principles couple an optical shape sensing fiber with an endograft. This may include an OSS system configured in the endograft that can be removed after deployment. Another embodiment includes an OSS system clipped onto the endograft after partial deployment. The OSS system may be pre-cannulated into the endograft to assist in aligning the endograft with side vessels. Other combinations and configurations are also contemplated.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for tracking and navigation of endografts and related accessories or tools with shape sensing enabled devices and systems is illustratively shown in accordance with useful embodiments. The navigation may be manual, computer-assisted or robotically performed. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from one or more shape sensing devices or systems 104. Optical sensing module 115 is configured to use the optical signal feedback (and any other feedback, e.g., electromagnetic (EM) tracking) to reconstruct deformations, deflections and other changes associated with a medical device or instrument, such as an endograft 102 (also referred to as a stent graft or covered stent), one or more guidewires 103, a handle(s) 105, deployment device 107, e.g., a catheter, a probe, a stiff guidewire, an endoscope, a stent-deployment system, a robot, an electrode, a filter device, a balloon device, or other medical component, etc.

A shape sensing system 104 includes one or more optical fibers 126 which are included in the system 104 in a set pattern or patterns. The optical fibers 126 connect to the workstation 112. The shape sensing system 104 may be included in one or more devices, such as in a catheter or deployment system (107), a guidewire (103), an endograft (102) or other medical component, etc. The OSS fibers 126 or OSS systems 104 are employed to provide a visual representation of an endograft, stent or markers, or through the use of pre-procedure planning used in combination with optical shape sensing for stent deployment. The present principles apply to any use of an optical shape sensing fiber 126 for navigation and deployment of a stent, stent-graft 102, or stent deployment system (deployment tool 107). The present principles can also apply to balloon catheters, clips, valves and other implantables.

In one embodiment, the fibers 126 of the OSS system 104 are integrated within the endograft 102. In other embodiments, the deployment tool, such as a guidewire 103 (which may also include a handle or handles 105), includes an OSS system (104), which can be employed for making physical measurements. The measurements may be employed for planning or for placement of an endograft 102 or stent. The endograft 102 or stent may include an OSS system 104 to provide shape, position and orientation information for the endograft 102 or stent.

Shape sensing system 104 may include one or more optical fibers 126. Shape sensing system 104 fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, strain causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter (enhanced and regular) in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

It should be understood that optical shape sensing may be performed in a plurality of ways and is not limited to FBGs or Rayleigh scatter techniques. For example, other techniques may include channels etched into the fiber, employing quantum dots for reflection, employing a plurality of separate fibers (e.g., 3 or more) instead of a single multicore fiber or other optical shape sensing techniques.

Workstation 112 includes a display 118 for viewing internal images of a subject (patient) or volume 131 and may include an image 134 (preoperative or intraoperative images) or an image 136 (OSS data) as an overlay or other rendering registered with the shape sensing system 104 in one or more of the components employed in the procedure. Display 118 may also permit a user to interact with the workstation 112 and its components and functions (e.g., touchscreen, graphical user interface, etc.), or any other element within the system 100. This is further facilitated by an interface 120 which may include a keyboard, mouse, a joystick, a haptic device, or any other peripheral or control to permit user feedback from and interaction with the workstation 112.

In one embodiment, an OSS fiber 126 or OSS system 104 or OSS enabled device 103, 105, 107, etc. is coupled to an endograft 102. The OSS fiber 126, OSS system 104, etc. (hereinafter referred to as an OSS system 104) is/are registered to a feature or features of the endograft 102. The OSS enabled device, fiber 126 or system 104 is removed after the endograft 102 has been placed.

By integrating an OSS enabled device 103, 105, 107, OSS fiber 126 or OSS system 104 to or within the wall of the endograft 102, geometric information about the endograft 102 may be collected and ultimately used to visualize the endograft 102. Considerations for including OSS include how the integrated device affects the mechanical performance of the endograft 102, how well the registration between OSS space and the identified tracked points is known and the effects on the clinical workflow.

Significant challenges integrating the OSS system 104 include interference with the clinical workflow caused by mechanical changes to the endograft 102 itself, and creating an integration that will not destroy an optical fiber (126) due to the extreme deformations experienced by the endograft 102 during packaging, delivery and deployment.

A registration module 130 is configured to register the OSS fiber 126 or system 104 to a physical structure (e.g., aneurysm, etc.), other OSS systems 104, images 134, 136, the endograft 102, etc. For shape recognition registration, a distinctive shape can be employed to obtain both position and orientation information from the fiber 126. If the fiber 126 takes a predefined and immutable path, the curvature and shape information of that path can be used to identify a unique image to fiber transformation to be stored in memory 116.

An image processing module 142 is configured to combine images (134) and OSS position data (image 136) for joint or separate display on the display 118. The OSS data 136 and the image data (from pre-operative or intraoperative images 134) can be registered and jointly displayed to assist in placement of the endograft 102 (or other stent or implantable device). An imaging system 110 may include a fluoroscopy system (x-rays) for collecting real-time visual information about positions of instruments or anatomical features. Other imaging modalities may also be employed. Images 134 collected with the imaging device 110 may be registered with the OSS data from OSS system 104.

During a conventional FEVAR procedure, a significant portion of time is spent cannulating the fenestrations of an endograft to ensure alignment with an underlying vasculature.

Figure 2B:
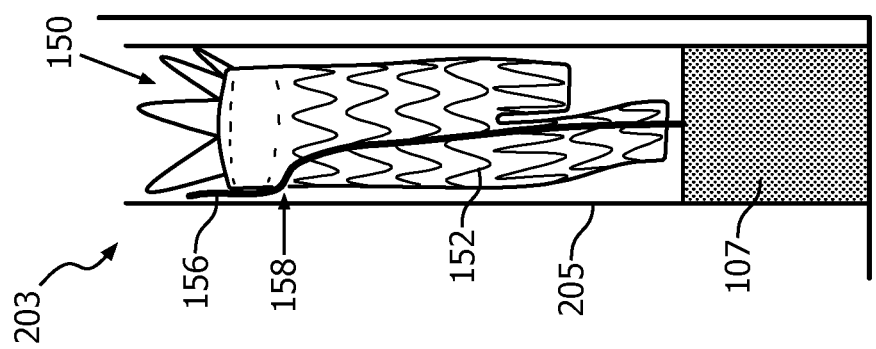
FIG. 2B is a diagram showing an endograft deployment package showing a pre-cannulated endograft in a sheath on a deployment device in accordance with one embodiment.
Figure 2A:
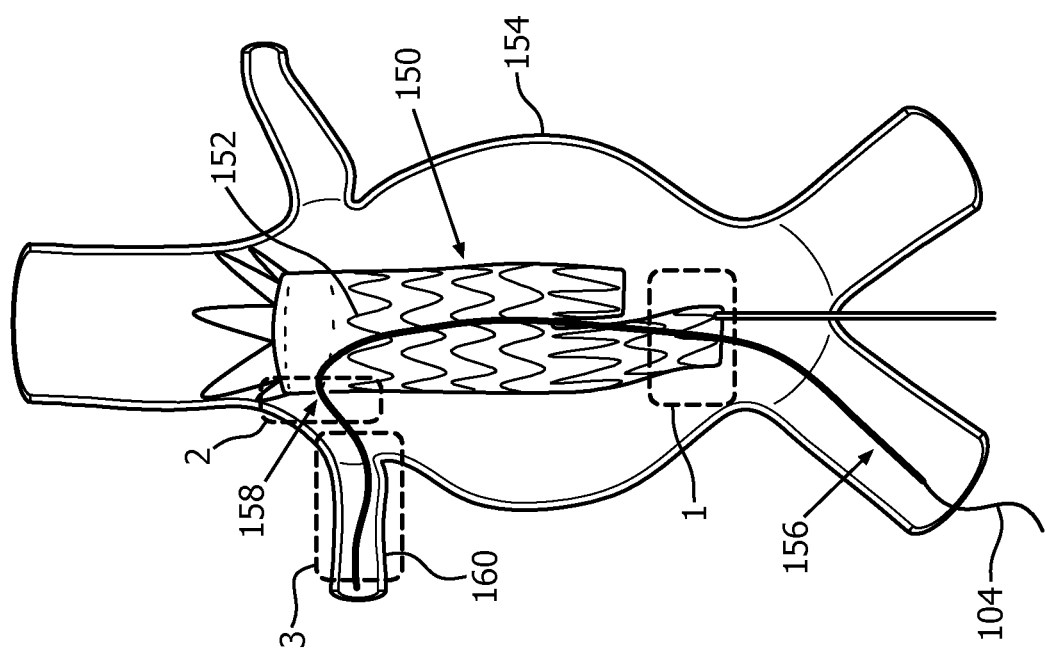
FIG. 2A is a diagram showing an endograft disposed in a blood vessel highlighting difficult to navigate areas and showing a pre-cannulation at a fenestration point in accordance with one embodiment.

Referring to FIG. 2A, an endograft 150 (or 102 in FIG. 1) includes an endograft structure 152 having a main body disposed within a vasculature 154 when deployed. The endograft structure 152 includes a deployable instrument 156 (such as a guidewire 103, FIG. 1, or the like). The deployable instrument 156 is OSS enabled and includes an OSS system 104 associated therewith. The instrument 156 is preferably pre-cannulated through a main body of the stent structure 152 at a position corresponding to a fenestration 158. The OSS system 104 associated with the deployable instrument 156 may be coupled to the instrument 156 or included within the instrument 156. The OSS system 104 measures shape, position and/or orientation of the deployable instrument 156, which is coupled to the fenestration 158. This can help with alignment of that fenestration 158 to a side vessel 160 or branch of the blood vessel 154. The OSS enabled deployable instrument 156 passes through the fenestration thus providing information which can be used to position the fenestration correctly. This may provide information to identify the position and orientation of other parts of the endograft structure.

There are three targets 1, 2, and 3 which need to be successfully navigated to place the endograft 150. The three difficult points of navigation of the guidewire (156) for cannulating, e.g., renal arteries 160 include: entering the contralateral or ipsilateral limb (target 1); finding and exiting the fenestration (target 2); and entering the renal or SMA artery (target 3). By registering patient anatomy to OSS space and a preoperative CT image (134, FIG. 1), OSS enabled guidewires 156 (103, FIG. 1) can be shape-sensed to provide radiation and contrast free visualization. Shape-sensed guidewires 156 may be packaged and pre-cannulated through fenestrations of the endograft 150.

This greatly reduces navigation time, as two of the three difficult navigation tasks will already have been accomplished in a pre-cannulated guidewire package 203 (FIG. 2B) with an OSS-enabled instrument 156 (guidewire).

Referring to FIG. 2B, the package 203 is illustratively shown for placing the endograft 150 for its deployment. The package 203 includes a sheath 205, which surrounds the endograft 150 and assists in maintaining the instrument 156 in place. The sheath 205 may be placed on a distal end of a deployment device 107 (such as a catheter or the like). The sheath 205 is retractable to deploy the endograft 150. The endograft 150 includes a pre-cannulated OSS enabled guidewire 103. This serves to greatly simplify the cannulation process and allow for visualization of endograft ports and openings which will serve to facilitate endograft deployment. This will be most applicable to commercially available FEVAR endograft systems. These devices 103 and/or 203 would be removed after deployment of the endograft 102 and would be easily withdrawn. By greatly reducing the navigation time and pre-cannulating side-vessels, the exposure time to x-rays and contrast dyes can be greatly reduced as well.

Figure 3B:
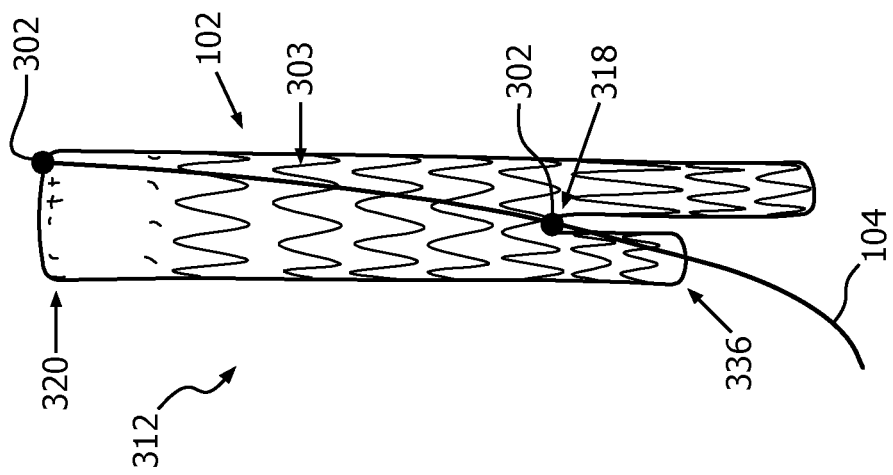
FIG. 3B shows an endograft having multiple attachment mechanisms attached to one optical shape sensing system in accordance with one embodiment.
Figure 3A:
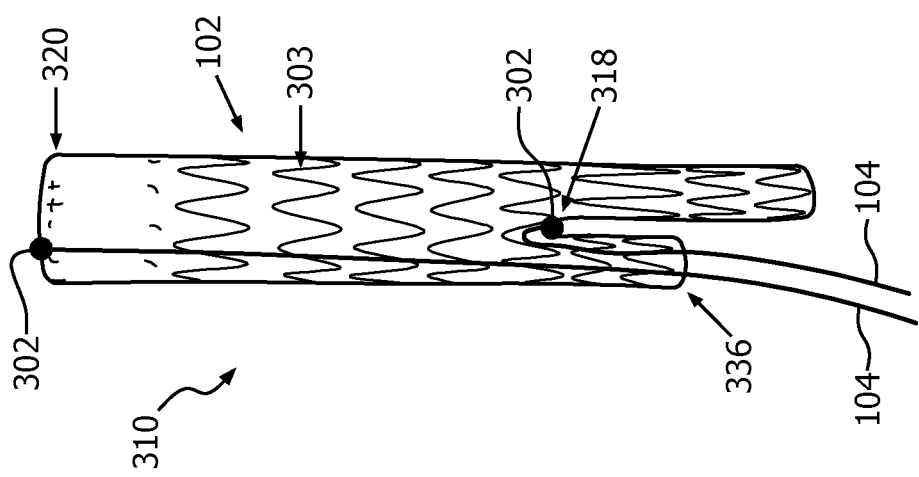
FIG. 3A shows an endograft having a single attachment mechanism attaching each of two optical shape sensing systems in accordance with one embodiment.

Referring to FIGS. 3A and 3B, two endograft clip systems 310 and 312 are depicted. Each system 310, 312 includes a stent structure 303 and one or more attachment mechanisms 302 configured to releasably attach to the stent structure 303.

One system 312 includes a multi-clip approach attaching to a proximal point 318 as well as a sealing ring 320 using a single OSS fiber 104. Another system 310 includes a multi-clip approach using two OSS fibers 104. A removable OSS enabled clip-on attachment mechanism 302 may be employed to track a discrete point(s) or feature(s) on an endograft 102, providing information to enable endograft visualization. While navigating these devices into the body and attaching them to different points on the endograft 102 (e.g., for a partially deployed endograft) is feasible, a clearly preferable alternative would be to have these devices attached to the endograft 102 before it was loaded into the deployment system. This would make multiple attachment points on a single device. An OSS enabled device or system 104 may include the attachment mechanism 302 at a distal tip, and would serve to provide tracking of a unique point on the endograft 102 for the purpose of creating a dynamic visualization of the endograft shape and position.

Depending on the desired application and accuracy of the visualization needed, different numbers of attachment points and locations may be employed. Some illustrative scenarios may include the following: 1) A most proximal position on endograft 102: Attaching to the portion of the endograft closest to the entry point can provide the least intrusive attachment point with minimal additional wires introduced to the inside of the endograft (which can already be quite crowded). 2) A most distal position on endograft: An anchor ring is the most position-critical portion of the endograft, as it is the only portion of the endograft which will be fixed to the anatomy. In addition, the anchor ring is the most rigid portion of the endograft and will provide valuable insight into the status of other portions of the endograft. 3) Multiple points of attachment: By combining the above options to create multiple points of attachment, the exact positioning of the endograft can be better known. These multiple points of attachment can be performed through individual shape sensing fibers 126 (FIG. 1), each with a single clip shown in system 310, or a single shape sensing fiber with multiple attachment mechanisms 302 shown in system 312 to attach at the various positions.

In the case of multiple attachment mechanisms or clips 302 with a same fiber or system 104 (system 312), it may be useful to have the fiber (104) translate (slide) through at least one clip position 302 to allow for expansion of the endograft 102. The fiber 104 can pass through a template shape at that clip position 316 as one way to determine the clip location along the fiber 104. A template shape is any curve or obstacle that can be employed to distinguish the shape of the fiber to identify a location (e.g., on the endograft 102).

Clips or attachment mechanisms 302 may be placed at any number of positions on an endograft 102. In a particularly useful embodiment, four anchor points that may be employed as attachment points for attachment mechanisms 302 may include the distal anchor ring 320, a fenestration (158, FIG. 2), a scallop or other geometric feature and/or a bifurcation junction 336. Each of these attachment points would likely need to be designed on an endograft line-specific basis, as individual endografts have different construction methods and styles. Types of attachment mechanisms 302 may include the following examples:

1) Jaw-type attachments: essentially a cable driven clamp that will grasp on to a feature of the endograft, like biopsy forceps. A locking mechanism would be able to attach this device such that it would remain in place without positive tension on the guidewire. 2) Hook type device: This device will have a shape that will interface with a feature on the endograft system and secure it, until the user advances the device to disengage. The hook-type device will likely need constant tension to ensure engagement. 3) Magnetic attachment: a magnetic device will attach to a ferromagnetic bead to track a position. 4) Capture tube: This device will envelop a small feature, likely an RO marker bead, and entrap it in a pocket in the device to be released later. Each mechanism may necessitate a slightly different anchor clip design and release mechanism. Other mechanisms are also contemplated.

The tracking information provided by these clip on attachment mechanisms 302 is targeted for use in endograft visualization. Registration between the endograft 102 and the clip/attachment mechanism 302 may be performed in a plurality of ways. These may include the following, for example. In the case where the clip 302 attaches to a specific point on the endograft 102, there will be a known relationship between the clip 302 and the endograft 102. The relationship between the clip 302 and the optical fiber (104) can be determined at the time of integration. As such, no specific registration step is necessary during the procedure. In the case where the clip 302 can attach to any point on the endograft 102, it may be necessary to determine the relationship between the clip 302 and the endograft 102. This can be done by taking two fluoroscopy images at different angles and identifying the clip position in each image (either automatically or through user input).

Following its use for navigation purposes, the clip 302 is released from the endograft 102. The release method will vary by the type of clip employed. A same clip may be employed for each of multiple cannulations of various fenetrations. In some cases, it may be necessary to release the clip 302 prior to final deployment of the endograft 102.

Disengagement from the endograft 102 may be accomplished with a pull-wire release, a sliding sleeve releasing an entrapped feature, unfastening a hook, etc.

Figure 4B:
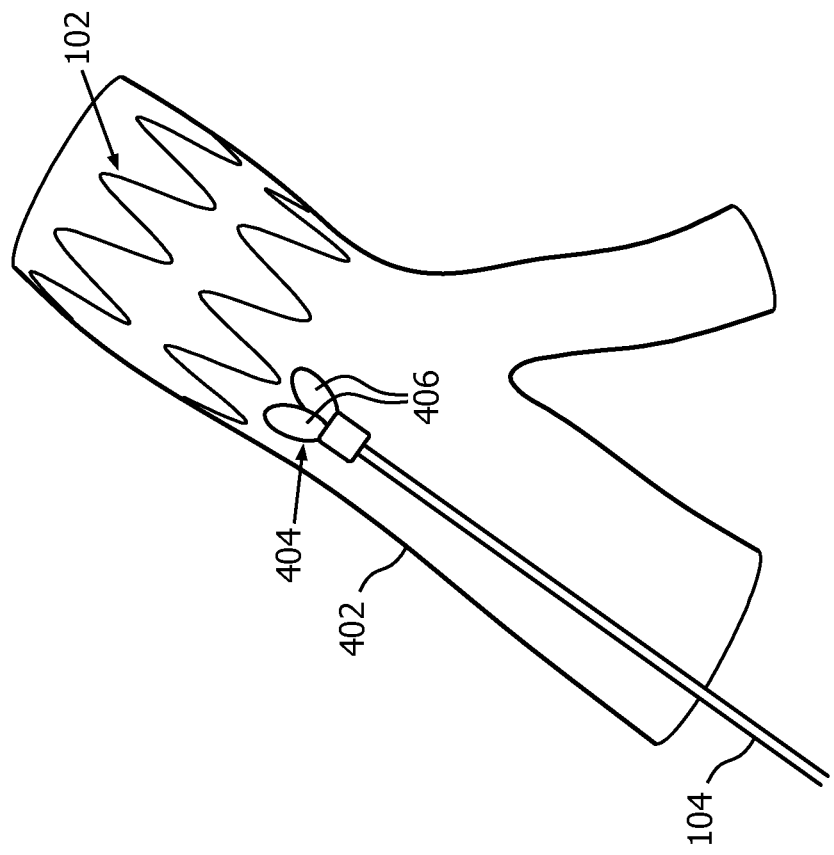
FIG. 4B shows the anchored endograft of FIG. 4A having the attachment mechanism released in accordance with one embodiment.
Figure 4A:
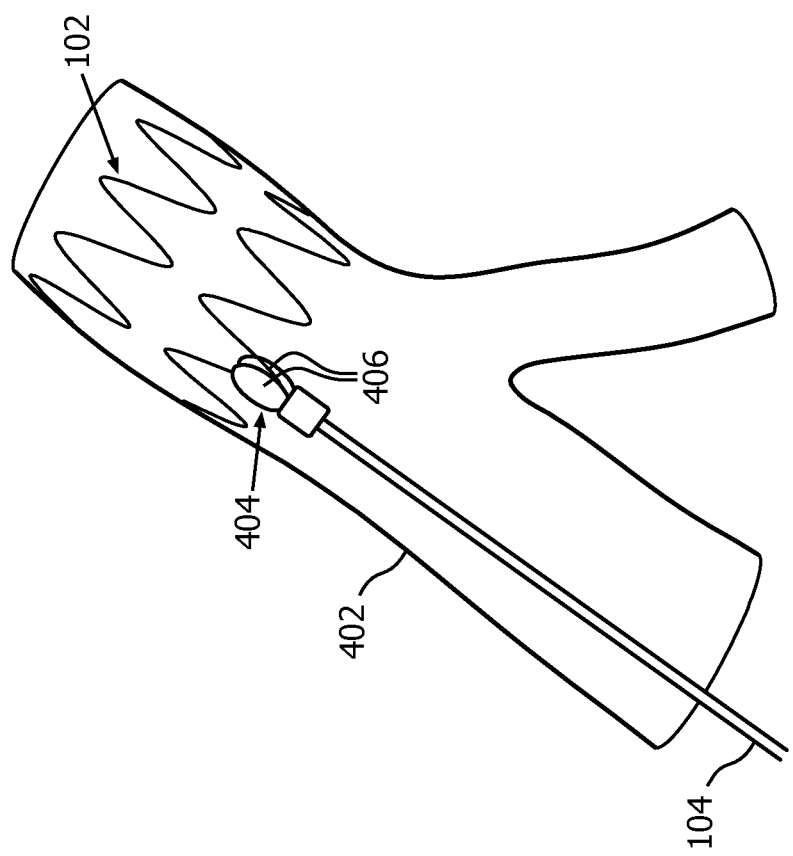
FIG. 4A shows an anchored endograft having an attachment mechanism attaching an OSS system to a proximal end thereof in accordance with one embodiment.

Referring to FIGS. 4A-4B, a diagram shows a clip/attachment mechanism 404 in accordance with one embodiment. The endograft 102 may be partially deployed near a target location in a blood vessel 402. The OSS tracked clip 404 is attached or clipped onto the endograft 102. The clip 404 may have closable jaws 406 that latch onto the endograft 102 when closed (FIG. 4A) but are releasable for removing the clip 404 (FIG. 4B). A display may be updated rendering the endograft 102 in the vasculature 402 using the OSS system 104 in the clip/attachment mechanism 404.

Figure 5:
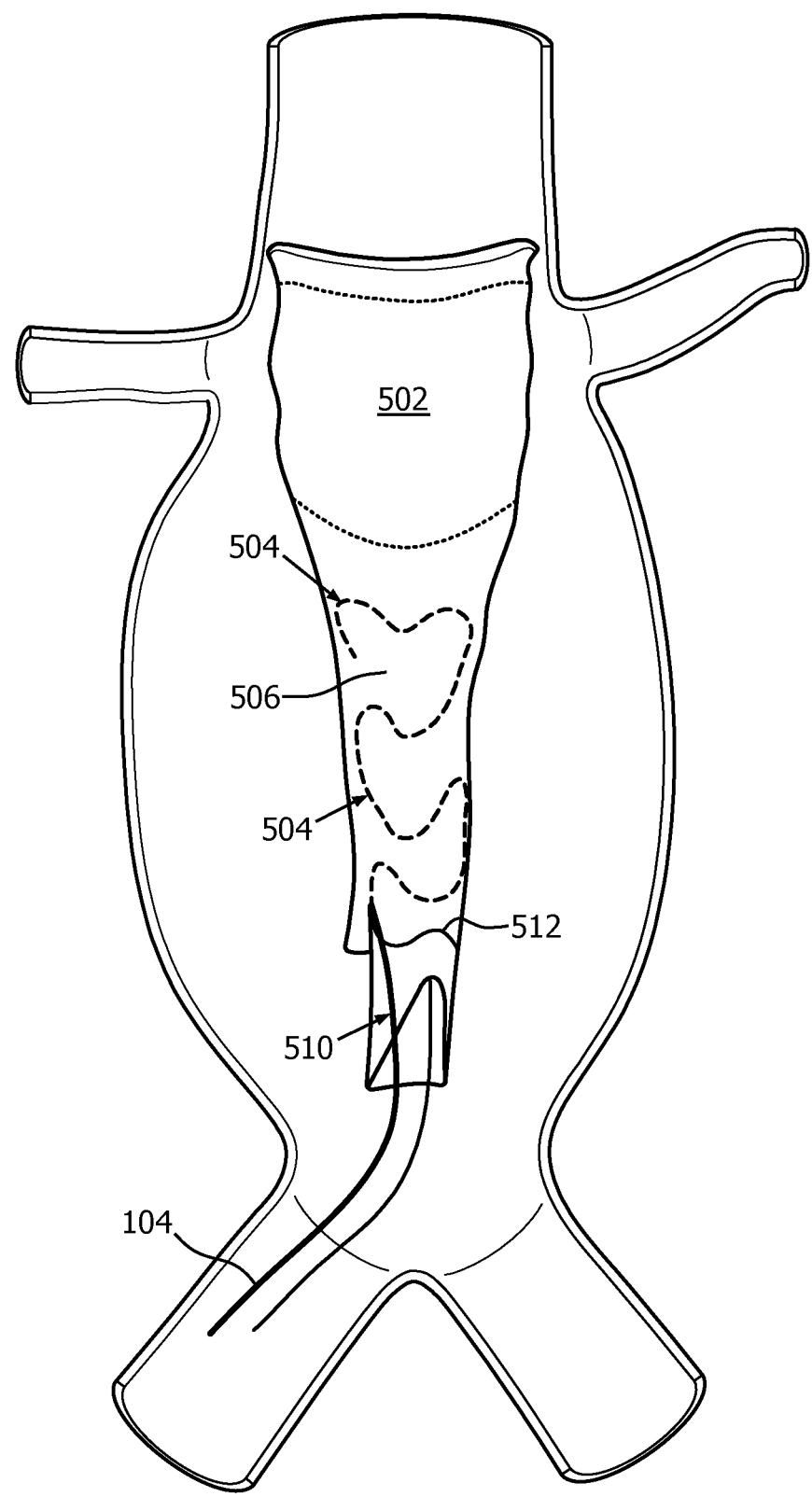
FIG. 5 shows an endograft having an OSS system routed through a wall of the endograft in accordance with one embodiment.

Referring to FIG. 5, another embodiment embeds an OSS system 104 in a wall 506 of an endograft 502. While attaching a fiber or fiber channel to the wall of the endograft 502 is challenging, this embodiment may provide the greatest amount of information, and permits the tracking of specific positions and rotations and other information regarding the deformation of the endograft 502. This approach will be especially useful when approaching complex, deformable endograft systems. In one embodiment, a fiber lumen 504 is embedded in a wall 506 of the endograft 502. The wall 506 may be made of fabric or other suitable material.

As endografts often include nitinol stent wires sewn into their body, one of these solid stent wires could instead be a hollow lumen 504, which may include an OSS fiber or fiber system 104. A removable lumen extension 510 may be attached to this hollow stent wire or hollow lumen 504 to complete the fiber path back to a launch position. If the deformation of a stent wire 512 is great enough to destroy an OSS fiber pre-deployment, the OSS fiber 104 could be retracted from the endograft 102 itself. Upon anchoring of the endograft 102, both the OSS fiber system 104 and the extension lumen 510 could be retracted. Other mechanisms may be employed to remove the OSS fiber as well.

In a particularly useful embodiment, the fiber path may include non-parallel segments (meandering, serpentine, zig-zag, etc.) such that the fiber can measure changes such as torsional and axial strain in the endograft 502.

Figure 6A:
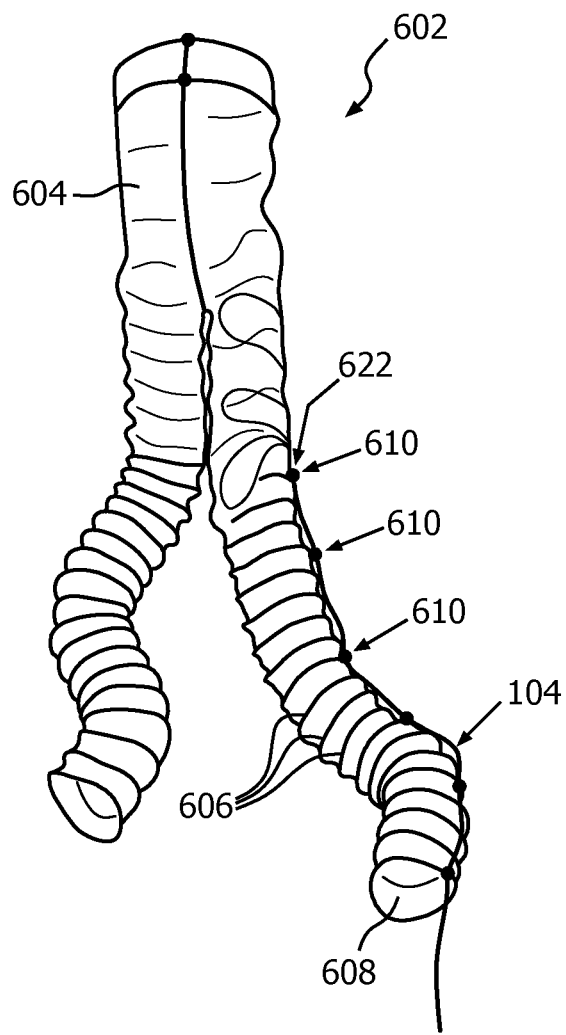
FIG. 6A shows an endograft having eyes for threading an OSS system therethrough in accordance with one embodiment.

Referring FIG. 6A, an endograft 602 (102, FIG. 1) includes a stent structure 604 having a lumen 608 with concentric supporting members 606 (e.g., rings). An eye 610 is formed within at least one of the concentric supporting members 606. An OSS system 104 passes through the eye 610, to be releasably secured to the stent structure 604 and to measure shape, position and/or orientation of the stent structure 604.

Figure 6B:
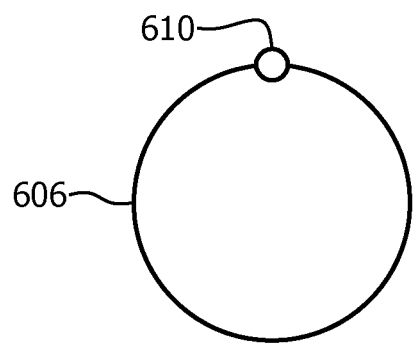
FIG. 6B shows a ring of the endograft of FIG. 6A showing an eye for threading the OSS system in accordance with one embodiment.

Referring to FIG. 6B with continued reference to FIG. 6A, a cross-section of a concentric supporting member or ring 606 is depicted. Ring 606 may include a feature or features (e.g., eyes 610) added to stent wires of the rings 606 where a fiber lumen or OSS system 104 could be passed through.

Features 610 added to the stentwires or rings 606 in the endograft 602 are employed to create a pathway 622 for an OSS enabled device or OSS system 104 to pass. This pathway 622 would permit tracking of the position of the stent rings 606 themselves, as well as clear insight into the torsion of the endograft 602 and the shape the endograft is conforming to. Another advantage of this integration structure is that the structure is less susceptible to damage from the packaging and deployment process. This is particularly suitable for endografts that have shown to have difficulties due to torsion.

In another embodiment, the OSS system 104 may be spirally disposed or helixed around a body of the endograft 602. This provides a more three-dimensional measurement of the endograft 602 by the OSS system 104.

Embodiments in accordance with the present principles provide the ability to improve outcomes and reduce contrast and radiation dose through the use of shape sensed devices for the location of a stent or the vaculature being stented. The OSS system permits navigation of the initial clip or attachment mechanism with minimal use of contrast and radiation. If a shape sensed guidewire is also employed in the main body graft, the shape information from that guidewire will also be available. The present principles apply to any use of an optical shape sensing fiber for navigation and deployment of a stent, covered stent, endograft or deployment system. These principles can be applied to any stent and/or balloon, or any other over the wire device employed in endovascular interventions. The approaches described herein are especially suitable for endograft systems, where the shape and position of the walls of the endografts have the potential for large deformations, displacements and torsions.

It should be understood that the present principles cover any of the applications where an endograft is deployed under fluoroscopic or other guidance including, but not limited to procedures, such as, e.g., endovascular aneurysm repair (EVAR), branch-fenestrated EVAR (BEVAR), percutaneous EVAR (PEVAR), thoracic EVAR (TEVAR), fenestrated EVAR (FEVAR), etc.

Figure 7:
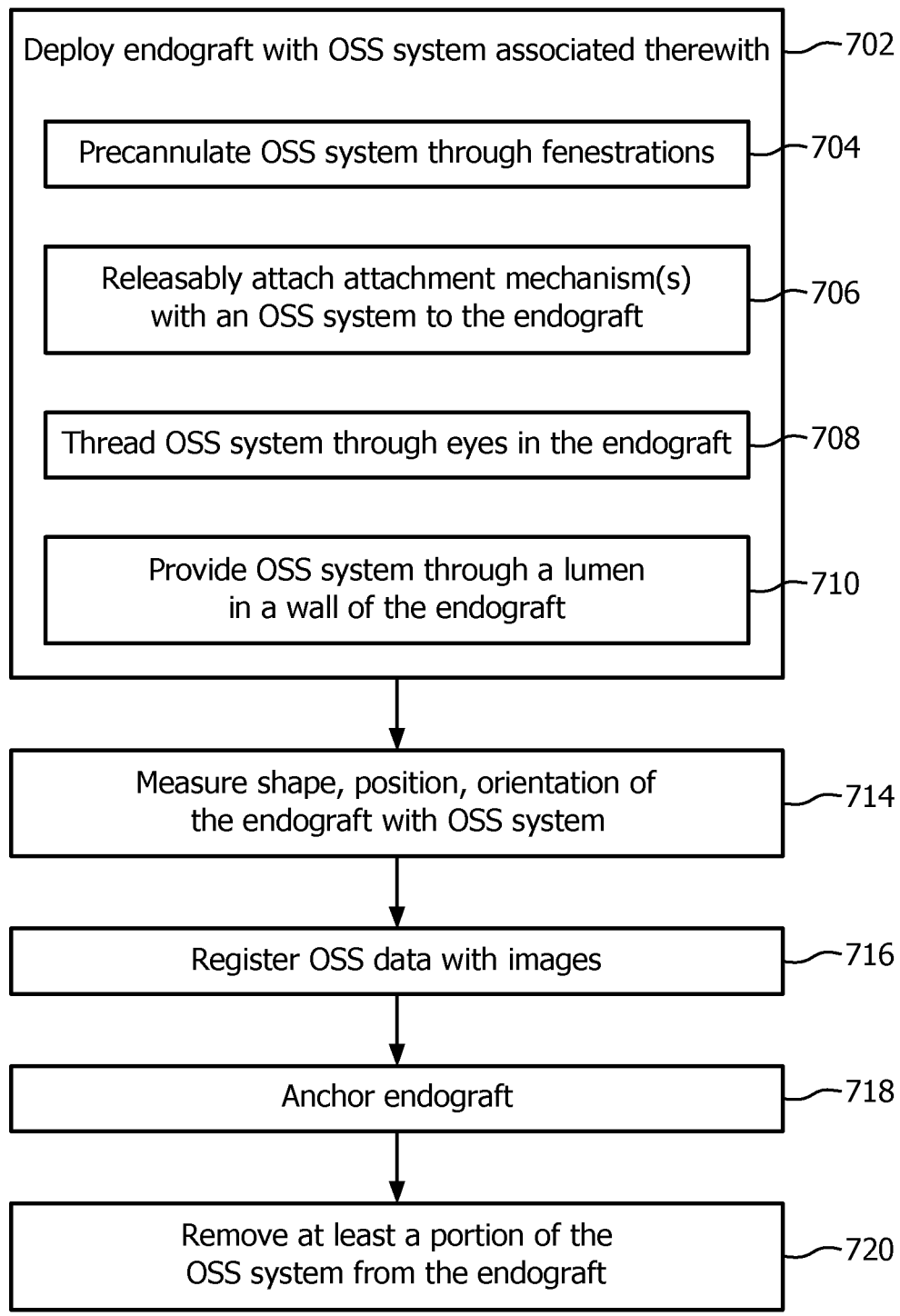
FIG. 7 is a flow diagram showing a method for endograft placement/deployment using an optical shape sensing system in accordance with illustrative embodiments.

Referring to FIG. 7, a method for endograft deployment is described and shown in accordance with illustrative embodiments. In block 702, at least one OSS system associated with an endograft is deployed. The OSS system may be releasable attached to the endograft in a plurality of ways and for different purposes, as illustratively described in the following.

In block 704, the at least one OSS system includes one or more pre-cannulated guidewires positioned corresponding to one or more fenestrations in the endograft. The fenestrations are aligned with side branches of the blood vessel using the at least one OSS system. The OSS-enabled guidewires, e.g., floppy guidewires, are removed in a later step.

In block 706, the at least one OSS system is releasably attached to the endograft by an attachment mechanism. The attachment mechanism is selectively releasable to remove the at least one OSS system in a later step.

In block 708, the endograft includes eyes formed within concentric supporting members. The at least one OSS system is threaded through the eyes. The eyes can provide a straight line, a curve or spiral (helix) about a body of the endograft. The at least one OSS system is removed in a later step.

In block 710, the endograft includes a lumen formed within a wall of the endograft, and the at least one OSS is provided within the lumen. The lumen may be formed in a retractable portion of the endograft and later removed by removing the retractable portion such that the retractable portion and at least a portion of the OSS system are removed in block 720.

In block 714, shape, position and orientation of the endograft are measured during deployment using the OSS system. In block 716, OSS data is registered with image data on a blood vessel where the endograft is placed. In block 718, the endograft is anchored in the blood vessel. In block 720, at least a portion of the OSS system may be removed from the endograft.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for endograft visualization with pre-integrated or removable optical shape sensing attachments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An endograft, comprising:
a stent structure;
at least one attachment mechanism configured to releasably attach to the stent structure; and
at least one optical shape sensing system having one or more optical fibers for generating optical shape sensing data, wherein said optical shape sensing system is coupled to the at least one attachment mechanism and is configured to measure at least one of shape, position or orientation of the stent structure based on the optical shape sensing data.

2. The endograft as recited in claim 1, wherein the at least one attachment mechanism includes a hook, a clip, a clamp, a magnet and a capture tube.

3. The endograft as recited in claim 1, wherein the at least one attachment mechanism is coupled at a distal end of the at least one optical shape sensing system.

4. The endograft as recited in claim 1, wherein the at least one attachment mechanism attached to the stent structure at attachment point of a geometric landmark.

5. The endograft as recited in claim 4, wherein the attachment point includes one or more of a ring of the endograft, a fenestration, a scallop or a bifurcation junction.

6. The endograft as recited in claim 1, wherein the at least one attachment mechanism is selectively releasable from the stent structure.

7. The endograft as recited in claim 1, wherein the at least one attachment mechanism includes a plurality of attachment points on the stent structure for at least one of the at least one optical shape sensing system.

8. An endograft, comprising:
a stent structure;
at least one deployable instrument pre-cannulated through a fenestration in the stent structure; and
the at least one deployable instrument including an optical shape sensing system having one or more optical fibers for generating optical shape sensing data, wherein said optical shape sensing system is configured to measure at least one of shape, position or orientation of the stent structure based on the optical shape sensing data and to align the fenestration with a branch of a blood vessel for placement of the endograft based on the optical shape sensing data.

9. The endograft as recited in claim 8, wherein the deployable instrument includes a guidewire.

10. An endograft, comprising:
a stent structure having a wall;
a lumen formed within the wall of the stent structure; and
an optical shape sensing system having one or more optical fibers for generating optical shape sensing data, wherein said optical shape sensing system is configured to pass into the lumen, to be releasably secured to the stent structure and to be configured to measure at least one of shape, position or orientation of the stent structure based on the optical shape sensing data.

11. The endograft as recited in claim 10, wherein the stent structure includes a retractable optical shape sensing portion wherein at least a portion of the optical shape sensing system can be removed.

12. The endograft as recited in claim 10, wherein the lumen is at least partially included in a hollow stent wire.

13. The endograft as recited in claim 10, wherein the lumen follows a path that extends along a plurality of different directions within the wall.

14. An endograft, comprising:
a stent structure having a lumen with concentric supporting members;
an eye formed with at least one of the concentric supporting members; and
an optical shape sensing system having one or more optical fibers for generating optical shape sensing data, wherein said optical shape sensing system is configured to pass through the eye, to be releasably secured to the stent structure and to be configured to measure at least one of shape, position or orientation of the stent structure based on the optical shape sensing data.

15. A method for endograft deployment, comprising:
deploying at least one optical shape sensing system associated with an endograft, said optical shape sensing system having One or more optical fibers;
measuring at least one of shape, position or orientation of the endograft during deployment using the at least one optical shape sensing system;
registering optical shape sensing data with image data on a blood vessel where the endograft is placed; anchoring the endograft in the blood vessel; and
removing at least a portion of the optical shape sensing system from the endograft.

* * * * *